United States Patent
Zhu et al.

(10) Patent No.: US 8,315,357 B2
(45) Date of Patent: Nov. 20, 2012

(54) RADIATION THERAPY INVERSE TREATMENT PLANNING USING A REGULARIZATION OF SPARSE SEGMENTS

(75) Inventors: Lei Zhu, Atlanta, GA (US); Lei Xing, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 248 days.

(21) Appl. No.: 12/924,832

(22) Filed: Oct. 6, 2010

(65) Prior Publication Data

US 2011/0085643 A1   Apr. 14, 2011

Related U.S. Application Data

(60) Provisional application No. 61/278,679, filed on Oct. 8, 2009.

(51) Int. Cl.
*A61N 5/10* (2006.01)
(52) U.S. Cl. .......................................................... 378/65
(58) Field of Classification Search ...................... 378/65
See application file for complete search history.

(56) References Cited

U.S. PATENT DOCUMENTS

| 7,391,026 | B2 * | 6/2008 | Trinkaus et al. | 250/363.02 |
| 7,899,517 | B2 * | 3/2011 | Kindlein et al. | 600/427 |
| 8,144,833 | B2 * | 3/2012 | Breedveld | 378/65 |
| 2005/0207531 | A1 | 9/2005 | Dempsey et al. | |
| 2009/0037150 | A1 * | 2/2009 | Craft et al. | 703/1 |

OTHER PUBLICATIONS

J. I. Serna et al., "Trade-off bounds for the Pareto surface approximation in multi-criteria IMRT planning," Phys. Med. Biol. 54, 2009, 6299-6311.*

Lei Zhu and Lei Xing, "Search for IMRT inverse plans with piecewise constant fluence maps using compressed sensing techniques," Med. Phys. 36(5), May 2009, 1895-1905.*

M. Monz et al., "Pareto navigation-algorithmic foundation of interactive multi-criteria IMRT planning," Phys. Med. Biol. 53, 2008, 985-998.*

David L. Craft et al., "Approximating convex Pareto surfaces in multiobjective radiotherapy planning," Med. Phys. 33(9), Sep. 2006, 3399-3407.*

Eduard Schreibmann et al., "Multiobjective evolutionary optimization of the number of beams, their orientations and weights for intensity-modulated radiation therapy," Phys. Med. Biol. 49, 2004, 747-770.*

H. W. Hamacher and K. H. Küfer, "Inverse radiation therapy planning—a multiple objective optimization approach," Discrete Applied Mathematics, 118, 2002, 145-161.*

* cited by examiner

*Primary Examiner* — Allen C. Ho
(74) *Attorney, Agent, or Firm* — Lumen Patent Firm

(57) ABSTRACT

A method of reducing a total number of beam segments in a dose distribution for a radiation therapy field is provided. The method includes providing a multiobjective radiation therapy treatment plan using a suitably programmed computer, where the multiobjective radiation therapy treatment plan includes a radiation beam dose performance objective and a fluence map sparsity objective in a given fluence function domain, and providing a Pareto frontier of tradeoff criteria between the beam dose performance and a total number of radiation segments (or sub-fields) of the multiobjective radiation therapy treatment plan using the suitably programmed computer, where an achieved set of radiation beam dose distributions associated with efficiency points of the Pareto frontier are evaluated using a clinical acceptance criteria, where a clinically acceptable radiation beam dose distribution having a smallest number of the multileaf collimator segments is a final solution for the multiobjective radiation therapy treatment plan.

11 Claims, 14 Drawing Sheets

(a)

(b)

(c)

(d)

(a)

(b)

RADIATION THERAPY INVERSE TREATMENT PLANNING USING A REGULARIZATION OF SPARSE SEGMENTS

CROSS-REFERENCE TO RELATED APPLICATIONS

This application claims priorty from U.S. Provisional Patent Application 61/278,679 filed Oct. 8, 2009, which is incorporated herein by reference.

STATENENT OF GOVERNMENT SPONSORED SUPPORT

This invention was made with Government support under contract W81XWH-05-1-0041 awarded by U.S. Army Medical Research Acquisition Activity Center and by contracts CA 098523 and CA104205 awarded by the National Institutes of Health. The Government has certain rights in this invention.

FIELD OF THE INVENTION

The present invention relates generally to methods and devices for radiation therapy. More specifically, it relates to radiation therapy treatment planning.

BACKGROUND OF THE INVENTION

Presently, a number of intensity modulation techniques are available, including fixed gantry IMRT planned using beamlet-based optimization (BBO) or direct aperture optimization (DAO), volumetric modulated arc therapy (VMAT), tomotherapy delivery (slice-by-slice delivery, binary collimator for modulation of beamlet intensity).

Each of these methods captures some aspect(s) of desired features of RT, but compromises in either dose distribution (fixed-gantry IMRT or VMAT) or inefficient delivery (tomotherapy). A truly optimal form of RT fully utilizing the technical capability of intensity modulation with efficient delivery is yet to be developed.

In intensity-modulated radiation therapy (IMRT), the treatment plan is selected from a large pool of physically feasible solutions by optimization of an objective function. The final solution depends on the choice of objective function and constraints applied to the optimization. Two commonly used approaches are beamlet-based and segment-based optimizations. In the traditional beamlet-based algorithms for the step and shoot IMRT, each beamlet intensity is an independent and continuous variable. For a fast calculation, the nonconvex physical constraints of the dose delivery are not included in the optimization. As a result, the optimized beamlet intensity map has a high complexity, and the number of segments for dose delivery is usually large after leaf sequencing. A large number of segments reduce not only treatment efficiency but also treatment accuracy due to increased patient motion during beam delivery and the involvement of irregularly shaped segments. Many attempts have been made to reduce the fluence map complexity by using various data smoothing techniques. These algorithms smooth the edges and help get rid of spiky behaviors of fluence maps. However, the overall shapes of the final fluence maps remain the same and, as thus, the solution so obtained represents only a small perturbation to the original unsmoothed plan and the reduction of the number of segments is usually rather limited.

Segment-based methods tackle the problem from the delivery aspect typically by enforcing a prechosen (often unjustified) number of segments for each incident beam and then optimizing the shapes and weights of the apertures. However, searching for an optimal solution by using segment based optimization is inherently complicated because of the highly nonconvex dependence of the objective function on the multileaf collimator (MLC) coordinates and the optimality of the final solution is not always guaranteed when an iterative algorithm is used.

An important characteristic that has not been utilized in most of inverse planning methods is that the IMRT solution space is highly degenerated in the sense that there are usually a large number of IMRT plans for the same prescription. While these plans yield similar dose distributions satisfying the prescription and constraints, the fluence maps of the plans can be dramatically different. Therefore, it is possible to stipulate constraints in the search of the optimal beamlet intensity such that the resultant number of segments is greatly reduced while the dose distribution is not severely deteriorated.

What is needed is, instead of directly including the nonconvex physical constraints in the optimization, which is computationally intensive and increases the probability of being trapped in local optimal solutions, an efficient method to achieve a global optimal solution only in a sparse space of fluence maps where the physical constraints are implied. What is further needed is a method that uses a beamlet intensity map delivered using a small number of segments that are piecewise constant and its derivative is sparse.

SUMMARY OF THE INVENTION

To address the needs in the art, a method of reducing a total number of beam segments of radiation therapy fields is provided. The method includes providing a multiobjective radiation therapy treatment plan using a suitably programmed computer, where the multiobjective radiation therapy treatment plan includes a radiation beam dose performance objective and a fluence map sparsity objective, and providing a Pareto frontier of tradeoff criteria between the beam dose performance and a total number of radiation beamlets of the multiobjective radiation therapy treatment plan using the suitably programmed computer, where an achieved set of radiation beam dose distributions associated with efficiency points of the Pareto frontier are evaluated using a clinical acceptance criteria, where a clinically acceptable radiation beam dose distribution having a smallest number of the radiation segments is a final solution for the multiobjective radiation therapy treatment plan.

In one aspect of the invention, the radiation therapy plan includes intensity modulated radiation therapy or arc therapy.

In another aspect of the invention, the radiation beamlets are disposed in a concatenated orientation during beam delivery.

In a further aspect of the invention, the efficiency points of the Pareto frontier are provided by a convex or non-convex optimization function that includes a regularization-based algorithm operated on a suitably programmed computer, where the regularization-based algorithm includes a totalvariation or objective term, a regularization term or a method of providing piece-wise connected fluence maps in an optimization objective function, and a multi-leaf collimator or a CyberKnife collimator aperture rectification algorithm. In one aspect, the piece-wise connected fluence map is a piecewise constant map, where the piece-wise connected map is a cone-shaped fluence, a constant slope or fixed spatial variation form.

According to one aspect of the invention, optimization of the multiobjective radiation therapy treatment plan includes using a convex optimization of an L-1 norm, a regularization term or a method for providing piece-wise connected fluence maps, where the convex optimization is disposed to enforce beam sparsity of the final solution, where the number of beam segments is minimized, and using a quadratic term or alike (other form of objective function) to quantify the radiation dose performance.

In a further aspect of the invention, an angular space delivery includes a combination of fixed-gantry beams and rotational arc beams.

In yet another aspect of the invention, the beamlets are determined using computed tomography (CT) images, treatment machine settings, and radiation beam geometry.

According to one aspect of the invention, the multiobjective radiation therapy treatment plan further includes a multi-leaf collimator (MLC) based IMRT delivery, where the MLC based IMRT delivery includes a uniformity constraint having a condition where an intensity map of a beam aperture is uniform inside an open area of the MLC and zero elsewhere, and a connectivity constraint having a condition where non-zero intensity areas of one the beam aperture are connected in a direction of leaf pairs of the MLC.

In a further aspect of the invention, the radiation source includes fixed-gantry IMRT or a hybrid of fixed-gantry IMRT and rotational arc therapy.

In a further aspect of the invention, the clinical acceptance criteria include inspection of dose volume histograms and dose distributions in a treatment plan.

DETAILED DESCRIPTION

Figure 1:
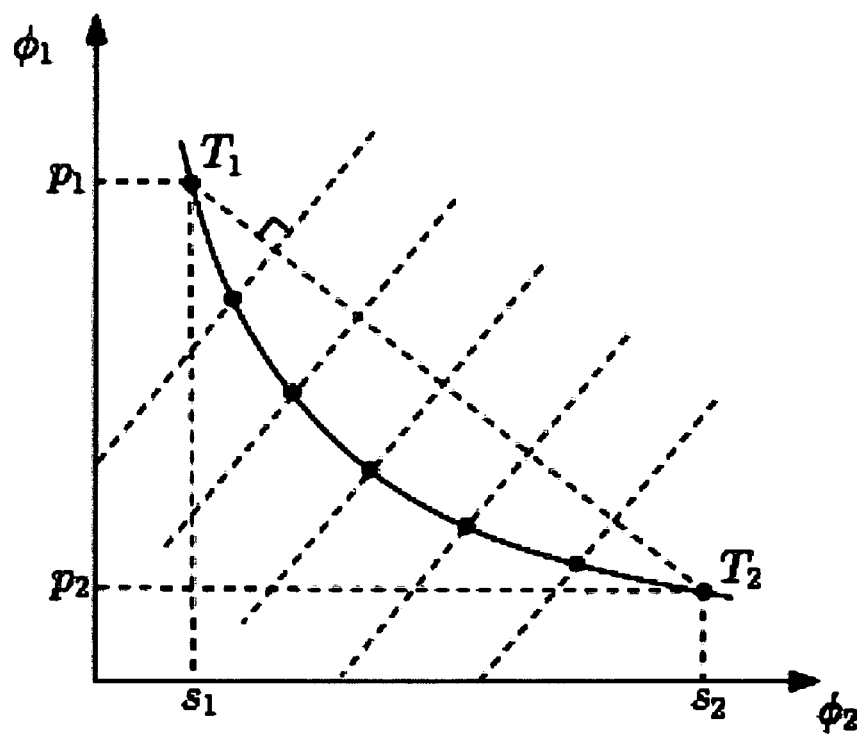
FIG. 1 shows a Pareto frontier of the multiobjective problem having T1 and T2 anchor points, according to one embodiment of the current invention.

An intensity-modulated radiation therapy (IMRT) field includes a series of segmented beams. It is practically important to reduce the number of segments while maintaining the conformality of the final dose distribution. Provided in this description is a quantified complexity of an IMRT fluence map by introducing the concept of sparsity of fluence maps and a formulated inverse planning problem into a framework of compressing sensing. In one aspect of the current invention, the treatment planning is modeled as a multiobjective optimization problem, with one objective on the dose performance and the other on the sparsity of the resultant fluence maps. A Pareto frontier is calculated, and the achieved dose distributions associated with the Pareto efficient points are evaluated using clinical acceptance criteria. The clinically acceptable dose distribution with the smallest number of segments is chosen as the final solution. The method is demonstrated in the application of fixed-gantry IMRT on a prostate patient. The result shows that the total number of segments is greatly reduced while a satisfactory dose distribution is still achieved. With the focus on the sparsity of the optimal solution, the method of the current invention is distinct from the existing beamlet- or segment-based optimization algorithms.

The algorithm according to one embodiment of the invention can be regarded as an application of compressed sensing method in signal processing. Briefly, compressed sensing is a technique for acquiring and reconstructing a signal that is known to be sparse or compressible. A mathematical manifestation of a sparse signal is that it contains many coefficients close to or equal to zero when represented in some domain. Effective utilization of this prior knowledge of the system (i.e., the sparsity of the signal to be processed) can used to reduce the required number of measurement samples (typically, this is determined by the classical Shannon-Nyquist theorem). Mathematically, IMRT inverse planning is analogous to the signal processing problem with the fluence maps being the "signal" to be detected for the given prescription doses. As mentioned above, inverse planning is an underdetermined problem and there are usually numerous fluence maps that are capable of yielding a clinically acceptable dose distribution. In this application, the sparsity of the derivative of the fluence maps makes compressed sensing a viable solution to the treatment planning.

Recovering or reconstructing sparse signals is generally a non-convex problem, and therefore the computation is intense. However, according to the current invention, a mathematically heuristic sparse solution can be obtained using a convex or non-convex optimization of an L-1 norm.

Beamlet-based optimization for inverse treatment planning is based on the linear relationship between the delivered dose distribution on the patient, d, and the intensity of the beamlets, x:

$$d = Ax, \quad (1)$$

where d is a vectorized dose distribution for a three dimensional volume, and the beamlet intensity x is a one dimensional vector that consists of row-wise concatenations of beamlet intensities for all fields. Each column of the matrix A is a beamlet kernel, corresponding to the dose distribution achieved by one beamlet with unit intensity. The beamlet kernels are pre-computed based on the CT images of the patient, the treatment machine settings, and the beam geometry. In the current invention, a voxel-based Monte Carlo algorithm (VMC) is used as the dose calculation engine.

For an efficient calculation, a convex function is used as an objective function in the optimization. If $\phi_1(x)$ is used, the square of the L-2 norm of the difference between the delivered dose and the target dose as the objective function of x, the treatment planning problem can now be expressed as follows: minimize $$\phi_1(x) = \sum_i \lambda_i (A_i x - d_i)^T (A_i x - d_i) \qquad (2)$$

subject to $x \geq 0$, where the index i denotes different structures, $\lambda_i$ is the relative importance factor; each column of the matrix $A_i$ is the beamlet kernel corresponding to the $i^{th}$ structure, and $d_i$ is the prescribed dose. The main variables used in this paper are summarized in Table I for reference.

TABLE I

Variable glossary.

| | |
|---|---|
| $A(A_i)$ | Matrix that relates the beamlet intensity to delivered dose |
| $d(d_i)$ | Delivered dose |
| N | Total number of beamlets, $N = N_u N_v N_f$ |
| $N_f$ | Number of fields |
| $N_t$ | Total number of segments of all fields |
| $N_u$ | Number of MLC leaf positions for each leaf |
| $N_v$ | Number of MLC leaf pairs per field |
| x | Beamlet intensity, the decision variable in the optimization |
| $\lambda_i$ | Importance factor associated with the ith structure |

The above optimization problem (2) does not consider dose delivery constraints of treatment machines. For MLC based IMRT delivery, two types of constraints on the segmented apertures are important. The first is the uniformity constraint, i.e., the intensity map of one beam aperture is uniform inside the MLC open area and zero elsewhere. The second is the connectivity constraint, i.e., the nonzero intensity areas of one beam aperture are connected in the direction of MLC leaf pairs.

The essence of compressed sensing methods is to utilize the prior knowledge that the signals of interest are sparse when represented in some domain. A fluence map is a summation of contributions from a series of segmented fields. If all the possible segments with different shapes are considered as the basis functions in a linear space, a fluence map with a small number of segments is a sparse presentation in such a space. Now the challenge is how to describe this sparsity mathematically and use it as an objective in the optimization.

According to one aspect of the invention, the sparsity of an actual fluence map is quantified based on the uniformity constraint of apertures. As a summation of uniform intensity maps with different shapes, an actual fluence map is a piecewise constant function, which can be "sparsified" by taking derivatives. Define a gradient operator as $$\nabla_{u,v} x(u,v) = |x_{u,v} - x_{u-1,v}| + |x_{u,v} - x_{u,v-1}|, \qquad (3)$$

where the variables u (v) is the row (column) index of the beam intensity for each field.

The sparsity of a fluence map can be evaluated as the summation of the absolute values of the gradients, defined as $$\phi_2(x) = \sum_{f=1}^{N_f} \sum_{u=2}^{N_u} \sum_{v=2}^{N_v} |\nabla_{u,v} x(u,v,f)|, \qquad (4)$$

where the beamlet intensity map x is parametrized by the variables u, v, and f The variable f is the field index. $N_u$ is the total number of possible MLC leaf positions for each leaf; $N_v$ is the total number of MLC leaf pairs per field; $N_f$ is the number of fields. For simplicity, the method according to the current invention assumes that each treatment field has a rectangular shape when it is fully open, and $N_u$ and $N_v$ do not change for different fields. Note that $\phi_2(x)$ is the L-1 norm of the gradient, i.e., a total-variation function, which is used as an objective function to encourage a piecewise constant solution.

The aperture constraints are non-convex and not included in the optimization step of the traditional beamlet-based methods, resulting in a large number of beam segments. In the method according to one embodiment of the invention, the number of segments are reduced without compromising the dose distribution by searching for solutions only in a sparse space of intensity maps. The sparsity of the intensity map is well correlated with the corresponding number of segments. The more sparse the optimized intensity map is, the less segments the leaf-sequencing algorithm derives. To enforce the sparsity on the optimized solution and therefore to reduce the number of segments, $\phi_2(x)$ is included as defined in Eq. (4) as a second objective function and reformulate the problem as a multiobjective optimization as follows:

minimize $$\begin{cases} \phi_1(x) = \sum_i \lambda_i (A_i x - d_i)^T (A_i x - d_i), \\ \phi_2(x) = \sum_{f=1}^{N_f} \sum_{u=2}^{N_u} \sum_{v=2}^{N_v} |\nabla_{u,v} x(u,v,f)| \end{cases} \qquad (5)$$

subject to $x \geq 0$.

Using an L-1 norm $\phi_2(x)$ as an objective, in fact, the problem is solved using compressed sensing techniques, which are able to find heuristic sparse solutions. The above formulation (5) is the main optimization framework proposed in this paper. The optimized beamlet intensity map, however, is close to but not exactly piecewise constant. Furthermore, the connectivity constraint due to the MLC hardware is not applied in the algorithm. A leaf-sequencing algorithm as in beamlet optimization is therefore needed to finally generate deliverable beam segments. The multiobjective optimization according to one embodiment of the invention, does not post special requirements on the leaf-sequencing step and any existing leaf sequencing algorithms can be used in combination with the proposed method.

The optimization of the multiobjective problem (5) is a trade-off between the dose performance and the total number of segments. If an upper limit constraint p is imposed on the first objective $\phi_1(x)$ and the minimization is carried out only on the second objective $\phi_2(x)$, the optimized solution gives the minimum number of segments that is required to achieve the dose performance defined by p. As the constraint p is relaxed or strengthened, the achieved minimum number of segments reduces or increases.

In order to obtain a final solution of the multiobjective optimization problem (5), the Pareto frontier is first calculated and then a solution is selected which satisfies the clinical acceptance criteria with the smallest number of segments. The main reason is that some of the clinical goals are non-convex and difficult to be included in the optimization as constraints. It is also difficult to find a proper value of upper limit p on the first objective $\phi_1(x)$, which is able to represent the clinical acceptance criteria. Visual inspections on the dose volume histograms (DVHs) and the dose distributions are therefore used to judge whether a certain plan is clinically acceptable.

The function $\phi_2(x)$ is not linear or quadratic. For an efficient calculation, optimization problem (5) is reformulated into an equivalent form as follows:

$$\begin{cases} \phi_1(x) = \sum_i \lambda_i (A_i x - d_i)^T (A_i x - d_i), \\ \phi_2(x) = e^T t \end{cases} \quad (6)$$

subject to $$x \succeq 0,$$
$$Bx - t \preceq 0,$$
$$Bx + t \succeq 0,$$

where e is an all-1 vector, with a size of $((N_u-1)N_v N_f + N_u(N_v-1)N_f) \times 1$, i.e., $e^T=(1,1,1,\ldots,1)$, $e \in R^{((N_u-1)N_v N_f + N_u(N_v-1)N_f) \times 1}$ the vector t is an intermediate variable with the same size as e; the matrix B is used to calculate the derivatives of x. Specifically, $$B = \begin{bmatrix} B_u \\ B_v \end{bmatrix}, \quad (7)$$

where $B_u$ is used to calculate the derivatives in the u direction:

$$B_u = \begin{bmatrix} C_1 & & & 0 \\ & C_2 & & \\ & & \ddots & \\ 0 & & & C_{N_v N_f} \end{bmatrix}. \quad (8)$$

$C_i$ are identical, with a size of $(N_u-1) \times N_u$:

$$C_i = \begin{bmatrix} -1 & 1 & 0 & \ldots & 0 & 0 \\ 0 & -1 & 1 & \ldots & 0 & 0 \\ \vdots & \vdots & \vdots & \ddots & \vdots & \vdots \\ 0 & 0 & 0 & \ldots & 1 & 0 \\ 0 & 0 & 0 & \ldots & -1 & 1 \end{bmatrix}. \quad (9)$$

$B_v$ is used to calculate the derivatives in the v direction:

$$B_v = \begin{bmatrix} D_1 & & & 0 \\ & D_2 & & \\ & & \ddots & \\ 0 & & & D_{N_f} \end{bmatrix}. \quad (10)$$

Di are identical, with a size of $N_u(N_v-1) \times N_u N_v$:

$$D_i = \begin{bmatrix} -1 & 0 & \ldots & 1 & 0 & \ldots & 0 \\ 0 & -1 & \ldots & 0 & 1 & \ldots & 0 \\ \vdots & \vdots & \ddots & \vdots & \vdots & \ddots & \vdots \\ 0 & 0 & \ldots & \ldots & \ldots & \ldots & 1 \end{bmatrix}. \quad (11)$$

On each row, −1 and 1 are separated by $N_u-1$ zeros.

In order to obtain the Pareto frontier, $\phi_2(x)$ is first fixed to a small value of $s_1$ and minimize $\phi_1(x)$ using the following quadratic optimization to obtain an objective value of $p_1$:
minimize $$\phi_1(x) = \sum_i \lambda_i (A_i x - d_i)^T (A_i x - d_i) \quad (12)$$

subject to $$x \succeq 0,$$
$$Bx - t \preceq 0,$$
$$Bx + t \succeq 0,$$
$$e^T t = s_1.$$

Repeat the optimization using a large $\phi_2(x)$ value of $s_2$ and obtain a minimized $\phi_1(x)$ value of $p_2$. Thus, two anchor points on the Pareto frontier, $T_1$ and $T_2$, are found, as illustrated in FIG. 1.

The selection of $s_1$ and $s_2$ determines the search range of the Pareto frontier. In one embodiment, these values are chosen empirically.

In order to calculate the complete Pareto frontier between the two anchor points, one solution is repeating the above optimization using different s values uniformly distributed between $s_1$ and $s_2$. This approach, however, does not achieve uniformly distributed data points on the Pareto frontier due to its curvature. To calculate Pareto efficient points more uniformly on the Pareto frontier, the values of $\phi_1(x)$ and $\phi_2(x)$ are minimized along lines perpendicular to the line connecting $T_1$ and $T_2$ as shown in FIG. 1. Mathematically, the optimization is changed to be as follows:
minimize $$\phi_2(x) = e^T t \quad (13)$$

subject to $$x \succeq 0,$$
$$Bx - t \preceq 0,$$
$$Bx + t \succeq 0,$$
$$\sum_i \lambda_i (A_i x - d_i)^T (A_i x - d_i) = g e^T t + h,$$

where the variable g is the slope of the lines perpendicular to the line $T_1 T_2$, $g=(s_2-s_1)/(p_1-p_2)$; the variable h is the intercept of these lines. Denote $h_1$ or $h_2$ as the intercept of the line passing through $T_1$ or $T_2$, $h_{1,2}=p_{1,2}-gs_{1,2}$. The optimization is repeated for different values of h, which are chosen uniformly between $h_1$ and $h_2$.

Note that the last constraint in the above formulation of optimization defines a non-convex solution set, which makes the problem challenging. Fortunately, it can be verified that this constraint can be changed to be convex without affecting the solution. The optimization becomes a linear programming with linear and quadratic constraints, as follows:
Minimize $$\phi_2(x) = e^T t \quad (14)$$

subject to $$x \succeq 0,$$

-continued $$Bx - t \leq 0,$$

$$Bx + t \geq 0,$$

$$\sum_i \lambda_i (A_i x - d_i)^T (A_i x - d_i) \leq g e^T t + h,$$

The algorithm according to the above embodiment has been tested on a prostate patient. The algorithm was implemented in MATLAB using the MOSEK optimization software package. The anchor points of the Pareto frontier were first calculated using a standard quadratic optimization routine provided in MOSEK with an interior-point optimizer according to the problem formulation (12). Other Pareto efficient points were calculated using a linear programming with linear and quadratic constraints as shown in Eq. (14).

Five fields were used at angles of 35°, 110°, 180°, 250°, and 325°, based on a standard clinical protocol for prostate patients. Each field targeted the center of the planning target volume (PTV) and contained 20×16 beamlets, with a beamlet size of 5×5 mm$^2$ at the source-to-axis distance (SAD). To save computation, the CT data were downsampled in the dose calculation, and the voxel size was 3.92×3.92×2.5 mm$^3$. The rectum, bladder, and femoral heads were included as sensitive structures. All the plans are normalized such that 95% of the PTV volume receives 100% prescribed dose (78 Gy).

To demonstrate the advantage of the current method, the existing beamlet-based planning algorithm is also compared using quadratic smoothing (L-2 norm regularization). For a fair comparison the algorithm is still implement as a multi-objective optimization and a quadratic term (the square of the L-2 norm) $\phi_3(x)$ is substituted for the L-1 norm $\phi_2(x)$. Mathematically, $\phi_3(x)$ is defined as $$\phi_3(x) = \sum_{f=1}^{N_f} \sum_{u=2}^{N_u} \sum_{v=2}^{N_v} ((x_{u,v} - x_{u-1,v})^2 + (x_{u,v} - x_{u,v-1})^2). \quad (15)$$

The Pareto frontier is calculated in a similar way as in the proposed algorithm.

Figure 2:
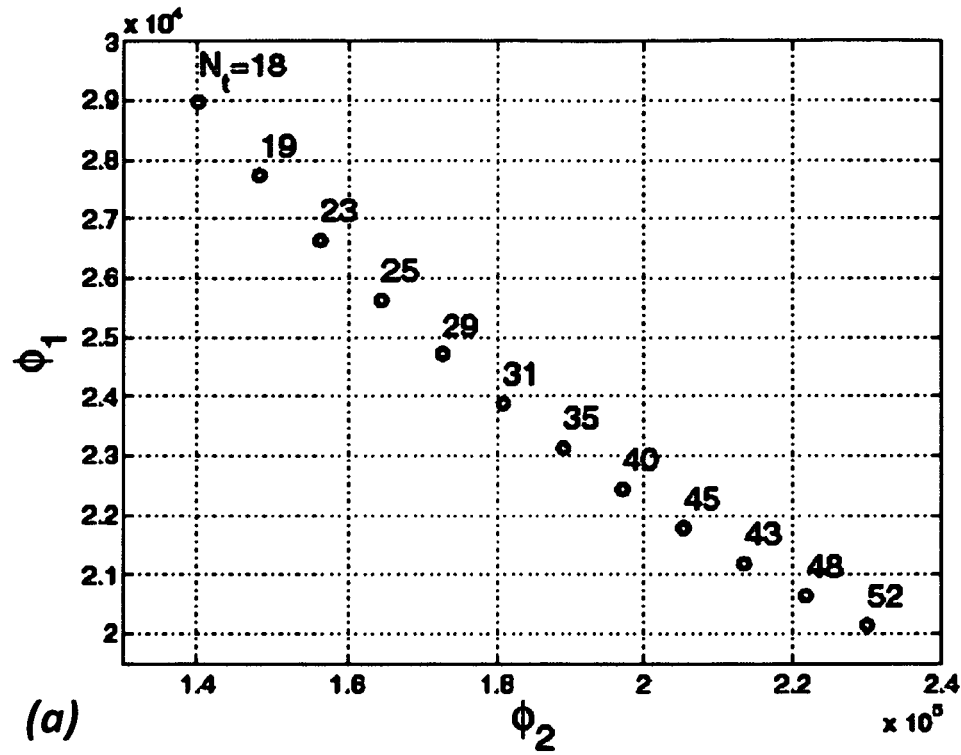
FIGS. 2a-2b show the calculated Pareto frontiers of the prostate plans using different objectives, according to one embodiment of the current invention.
Figure 2:
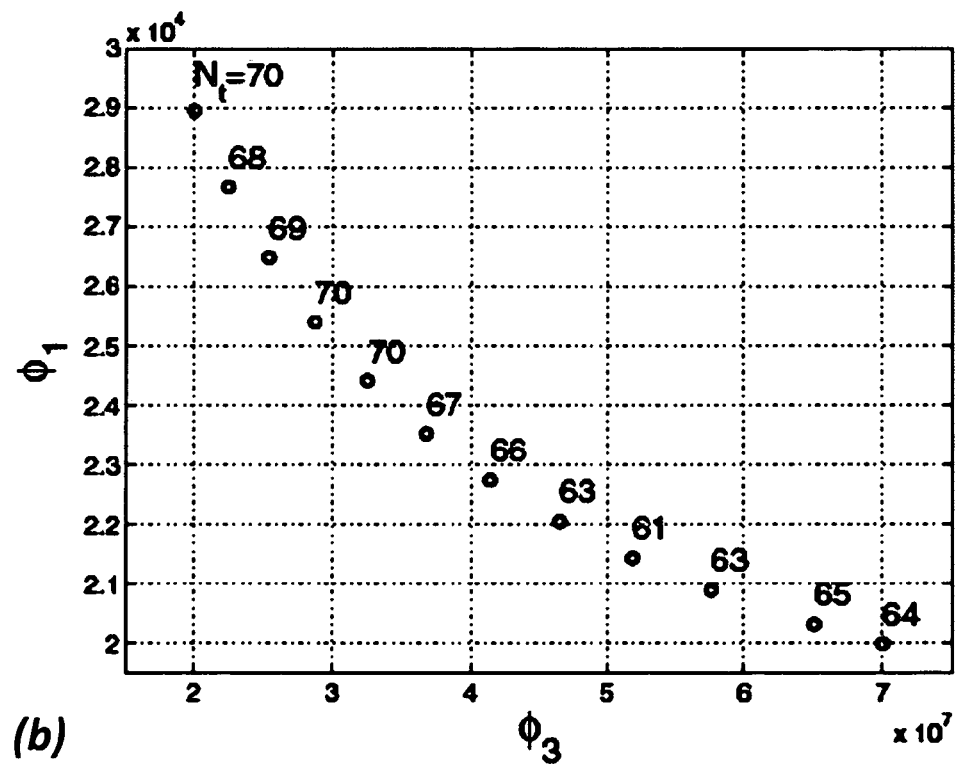

FIGS. 2a-2b compare the calculated Pareto frontiers of the prostate plan. Using the algorithm of the current invention with an L-1 norm as one objective, each Pareto efficient point of FIG. 2a took about 2 min on average on a 3 GHz PC to compute.

The number of segments ($N_t$) corresponding to each Pareto efficient point after applying a leaf-sequencing algorithm is also marked on the plot. As discussed earlier, in general, a small (large) $\phi_2(x)$ value on the Pareto frontier achieves a small (large) number of segments, while the dose distribution is degraded (improved), as indicated by the increase (decrease) in the $\phi_1(x)$ value. However, since the L-1 norm objective in the algorithm of the invention only implies the uniformity constraint of the apertures and the connectivity constraint is enforced by the subsequent leaf sequencing, the above relationship is not exactly monotonic. As shown in FIG. 2a, in some local areas (where $N_t$=45, 43), a larger $\phi_2(x)$ value achieves a smaller number of segments.

Figure 3:
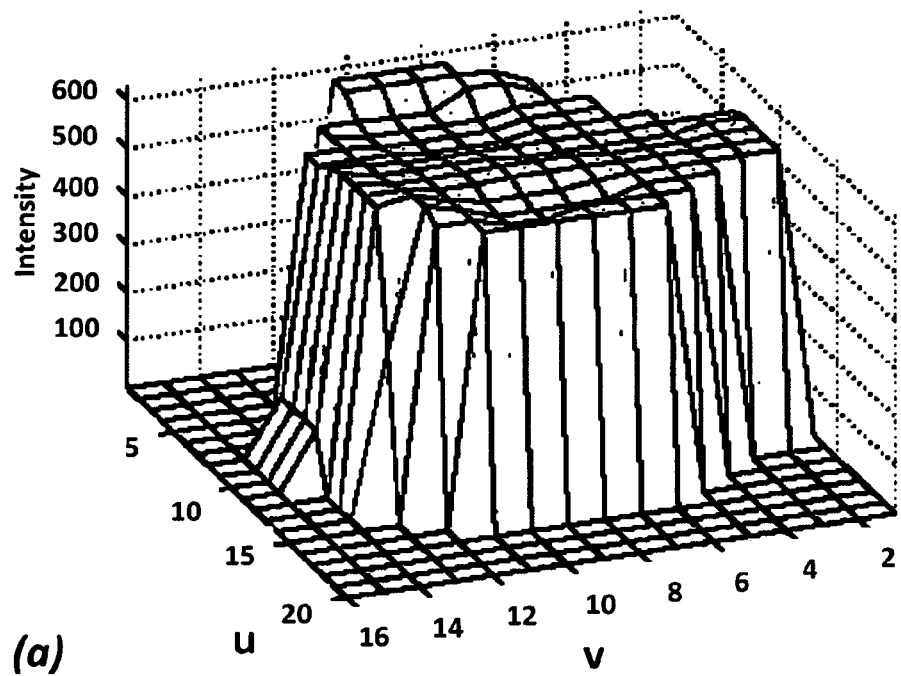
FIGS. 3a-3b show the optimized fluence maps for the fifth field using the L-1 norm and the L-2 norm in the optimization, according to one embodiment of the current invention.
Figure 3:
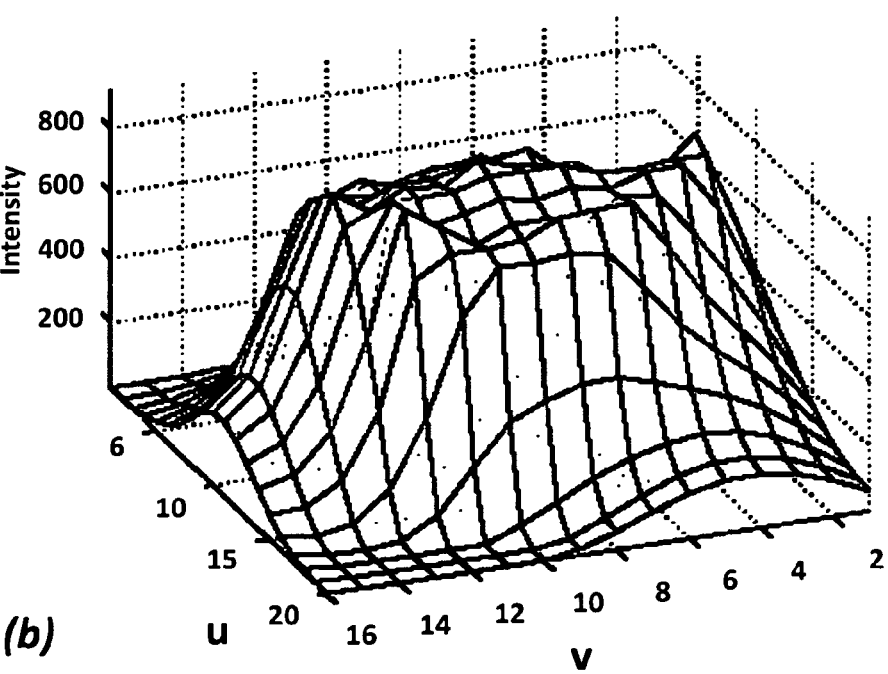
Figure 4:
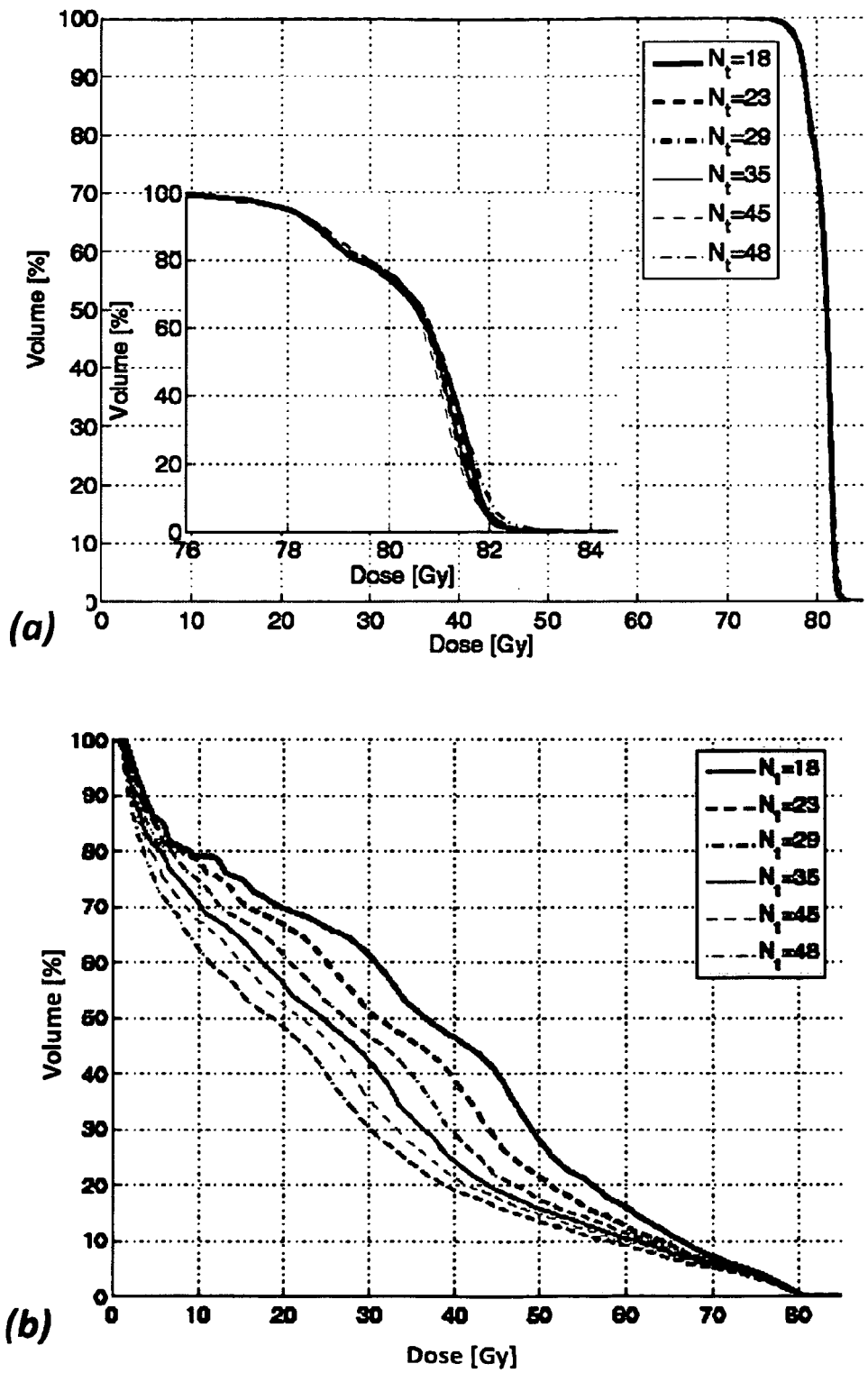
FIGS. 4a-4e show the dose volume histograms (DVHs) of the prostate plans corresponding to every other Pareto efficient point in FIG. 2a, according to one embodiment of the invention.
Figure 4:
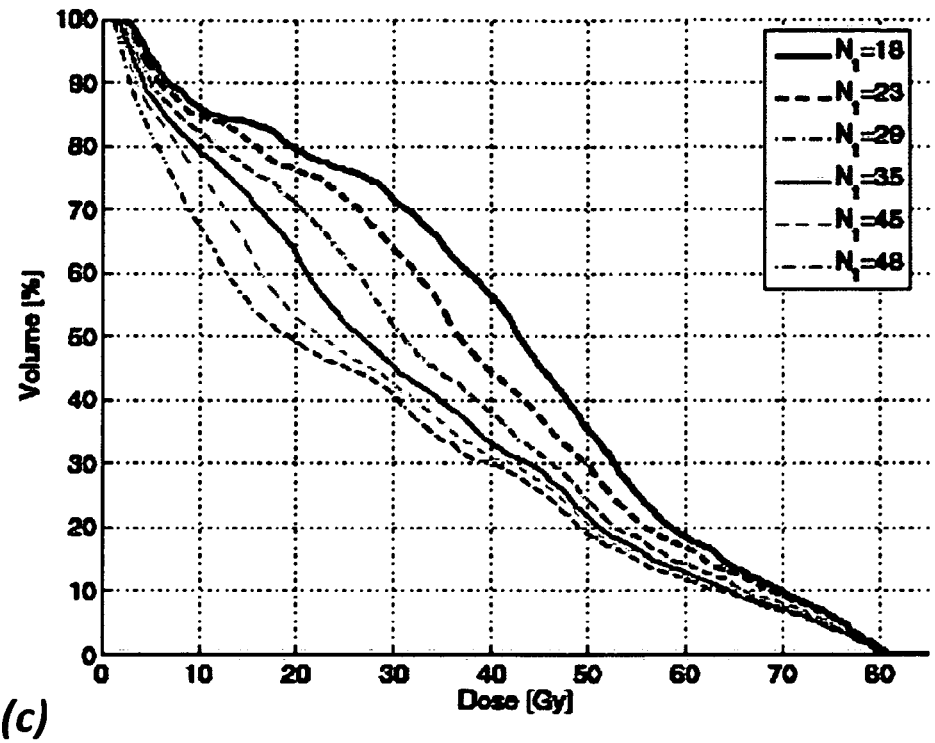
Figure 4:
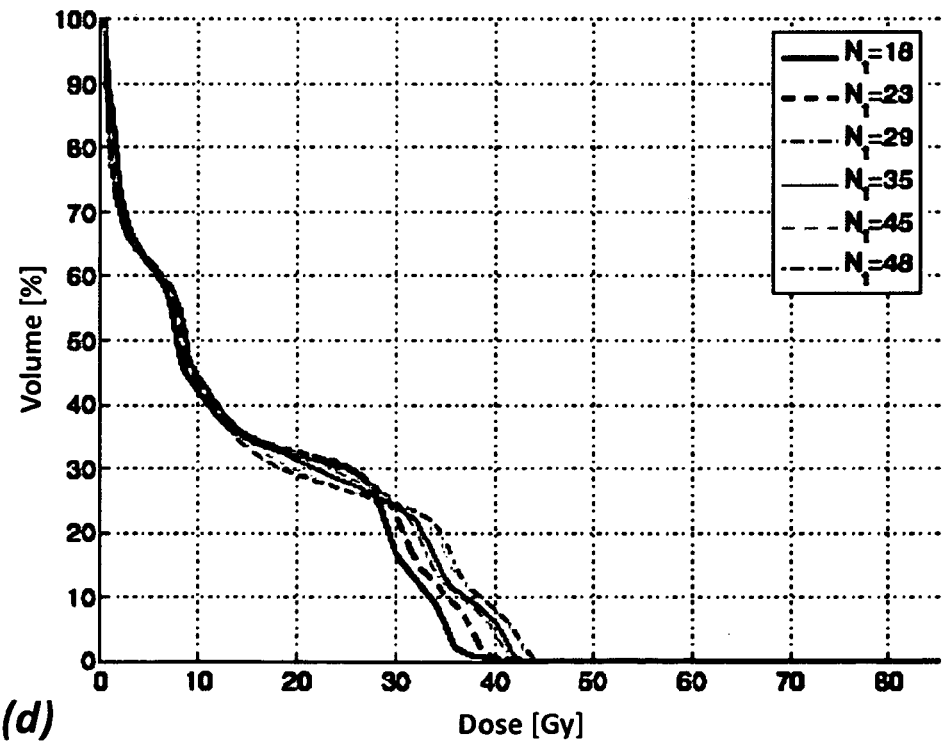
Figure 4:
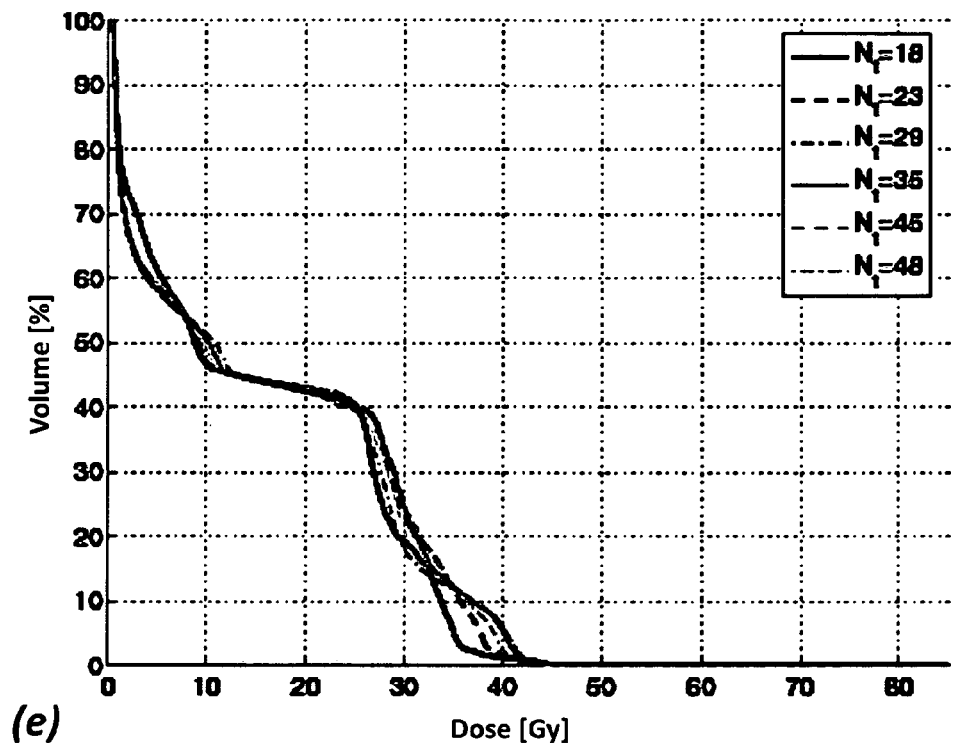
Figure 5:
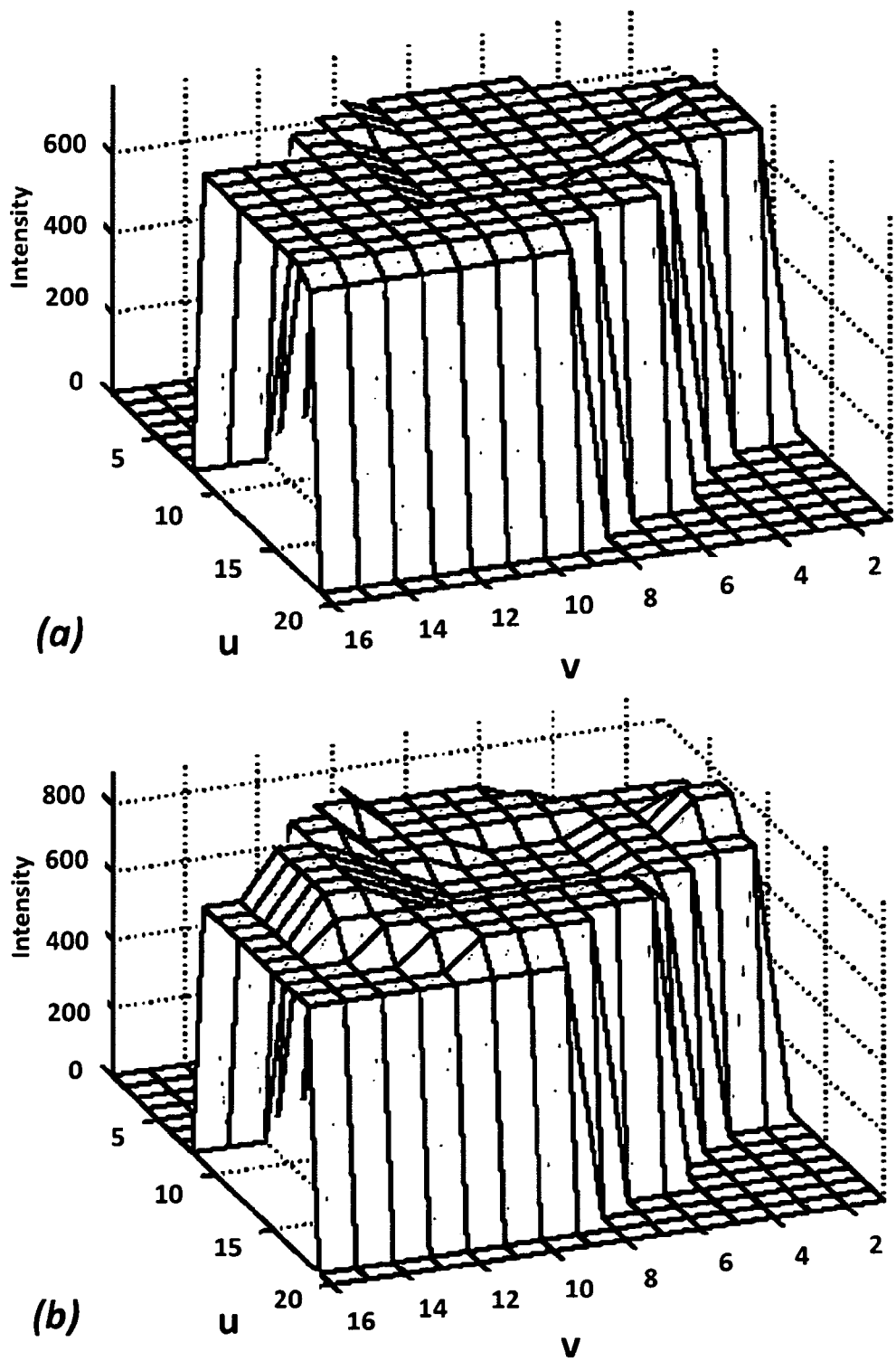
FIGS. 5a-5f show the actual fluence maps of the second field for different total numbers of segments, according to one embodiment of the invention.
Figure 5:
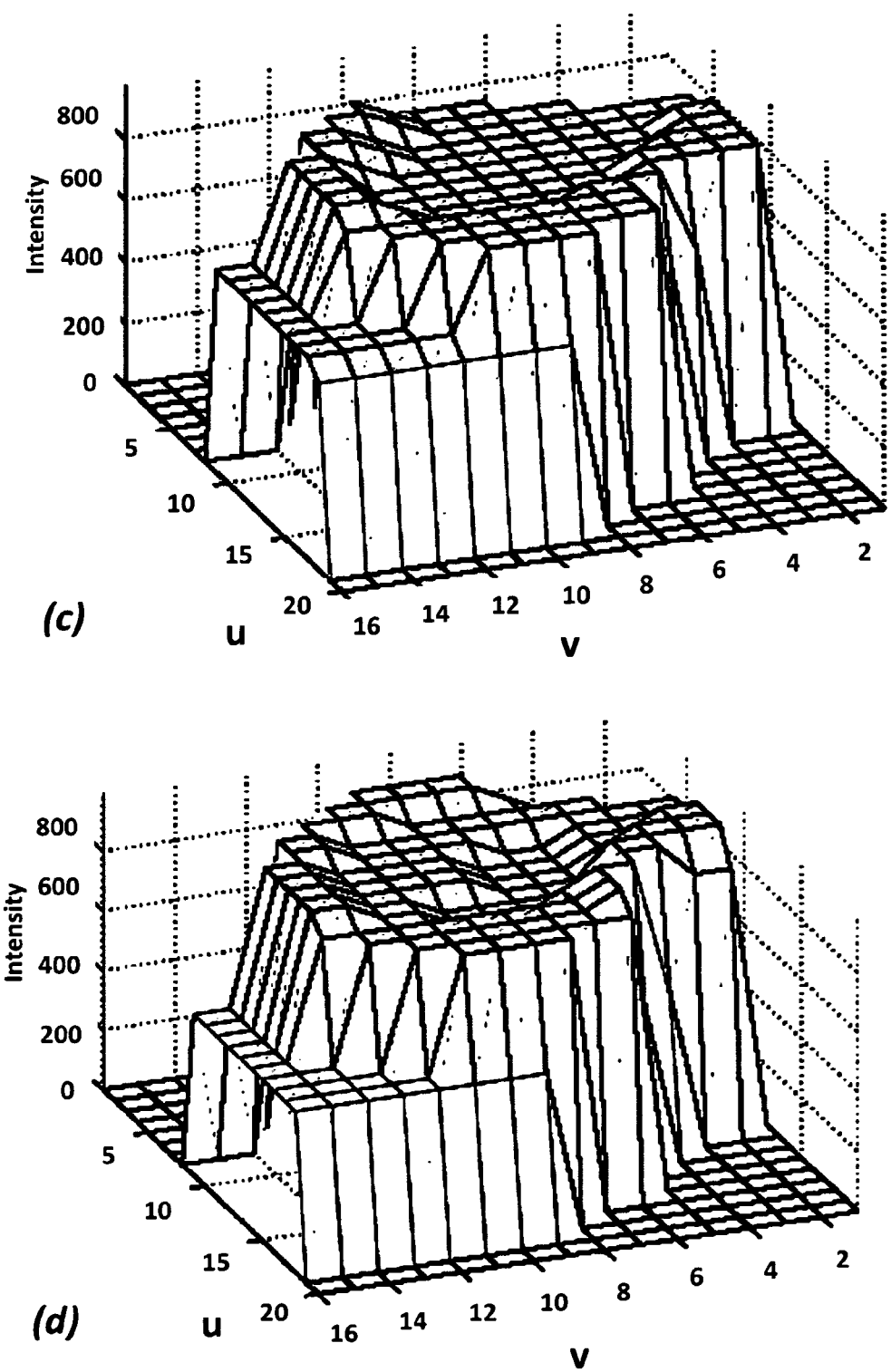
Figure 5:
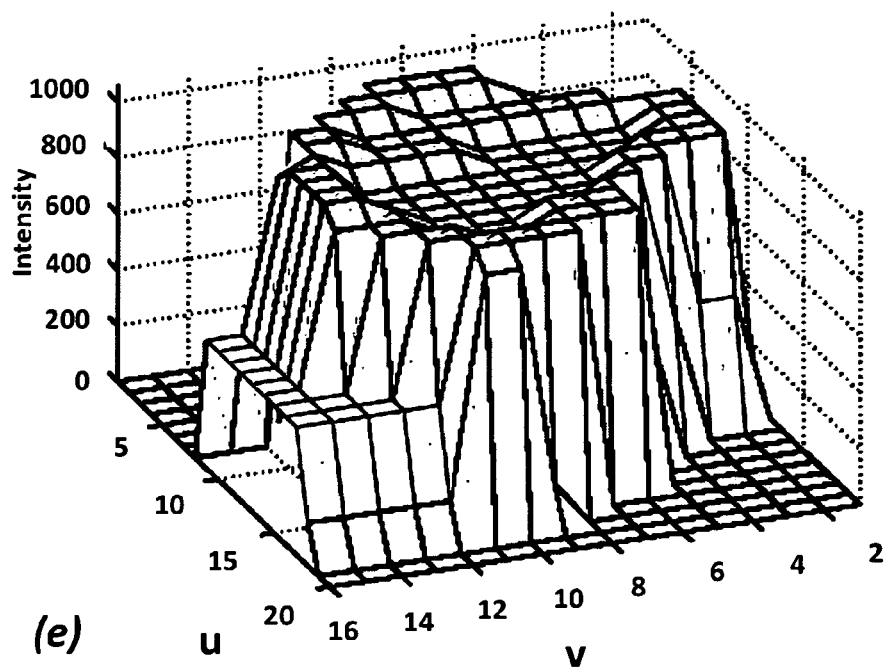
Figure 5:
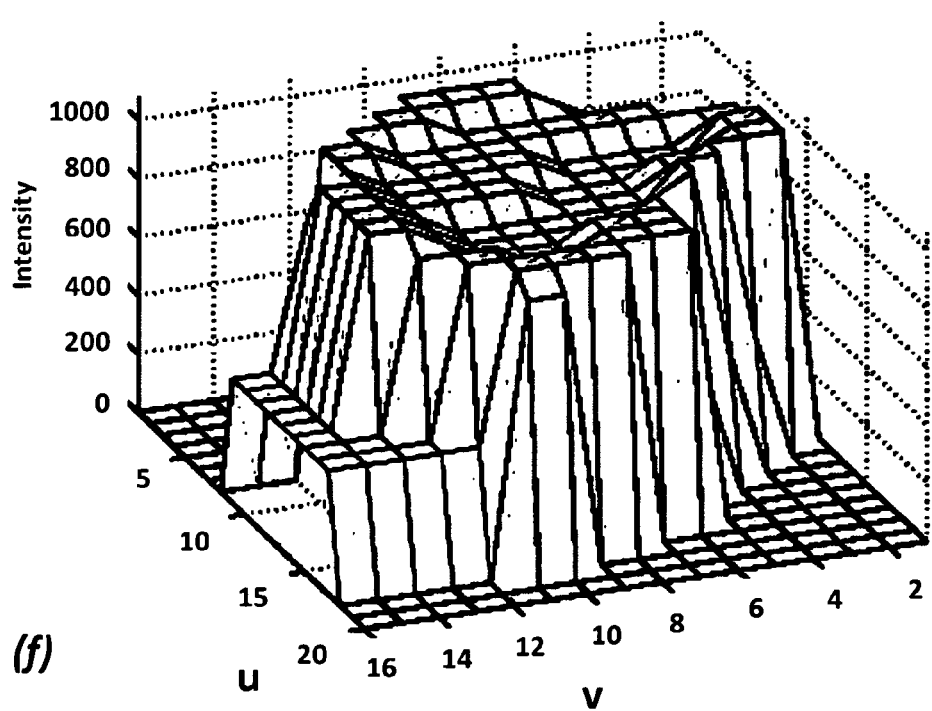
Figure 6:
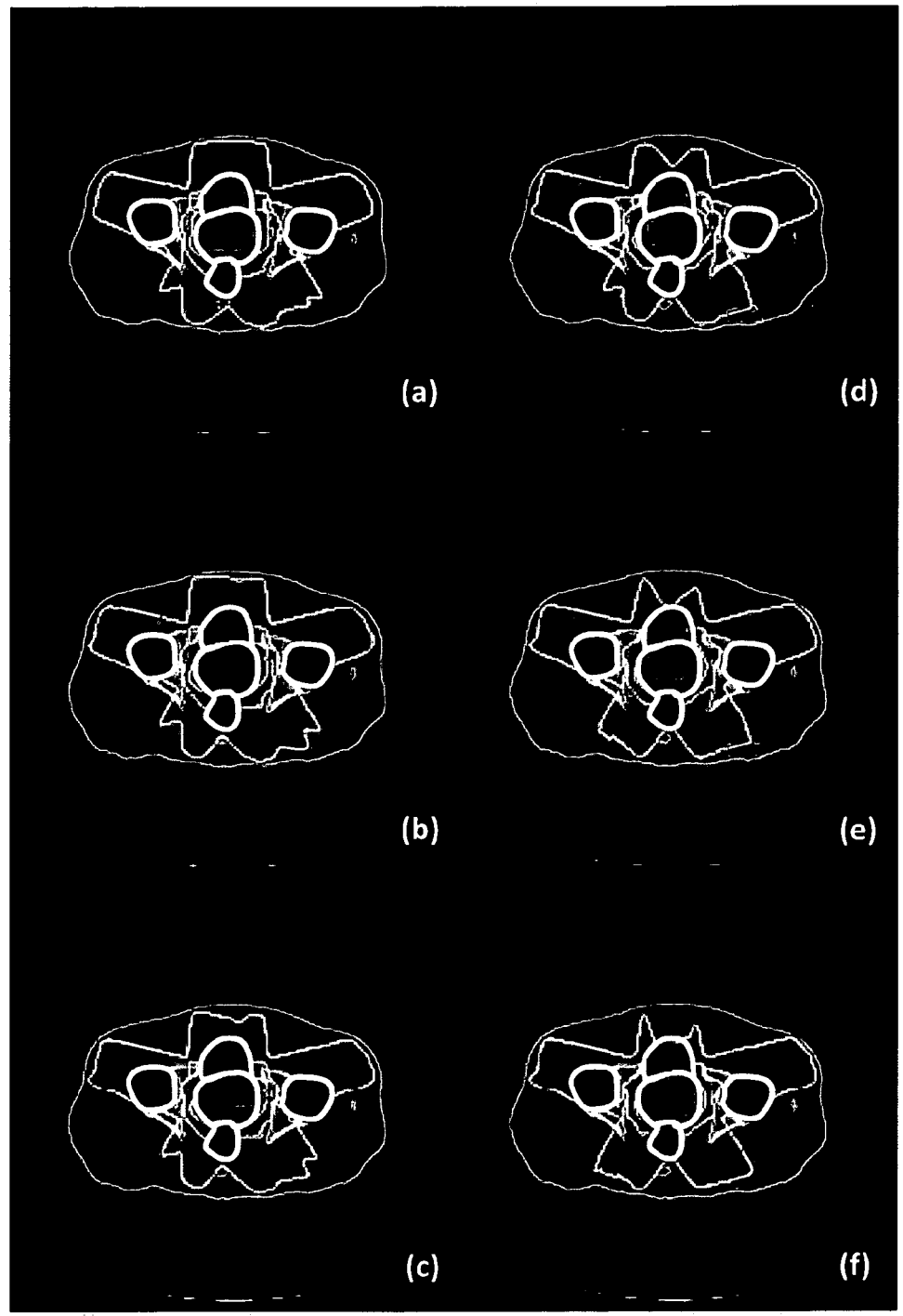
FIGS. 6a-6f show isodose distributions using different numbers of segments, according to one embodiment of the invention.

The calculated Pareto frontier using an L-2 norm square ($\phi_3(x)$) as one objective is shown in FIG. 2b. Each Pareto efficient point is equivalent to a beamlet-based optimal plan using quadratic smoothing. For a better comparison, the algorithm parameters are tuned such that the Pareto frontiers shown in FIGS. 2a and 2b have roughly the same range of $\phi_1(x)$ values. It is seen that, while the dose distribution performance is similar (as indicated by the close $\phi_1(x)$ values), the algorithm of the invention using an L-1 norm is able to achieve a total number of segments much smaller than that using an L-2 norm. It is also worth noting that as the quadratic smoothing gets stronger ($\phi_3(x)$ values get smaller), the total number of segments of the optimized plan does not decrease. This indicates that although quadratic smoothing is able to reduce the complexity of the fluence maps, it smoothes the edges of the maps and does not efficiently reduce the number of beam segments. To further support the above argument, FIGS. 3a-3b show the optimized fluence maps for the fifth field using the L-1 norm and the L-2 norm in the optimization. Both plans achieve almost the same dose distribution performance. However, using an L-1 norm as one objective achieves a nearly piecewise constant fluence map and only four segments are needed for this field. Instead, using an L-2 norm achieves a much smoothed fluence map and for this field, the resultant number of segments after leaf sequencing is 12.

FIGS. 4a-4e show the dose volume histograms (DVHs) of the prostate plans corresponding to every other Pareto efficient point in FIG. 2a. Each subfigure shows the DVH for one structure as $N_t$ changes. Since the plans are normalized based on the dose distribution on the planning target volume (PTV), the DVHs of the PTV are very similar for different $N_t$. However, more organ at risk (OAR) volume is spared as $N_t$ increases. FIGS. 5a-5f show the actual fluence maps of the second field for different total numbers of segments. As the number of segments increases, the complexity of the actual fluence map increases and the plan performance, especially the avoidance of the OARs, improves. The improvement slows down when the number of segments reaches a certain level. These plans are evaluated using clinical acceptance criteria and the results are summarized in Table II. The monitor units (MUs) per 2 Gy fraction are also listed for each plan. The plan is satisfactory when the segment number is not less than 35, and the result using 35 segments is chosen as the final solution. Using the Eclipse planning system on the same patient data, the total number of segments is 61. The method according to the invention, significantly reduces the number of segments without compromising the clinical performance of the treatment plan. The isodose distributions using different numbers of segments are shown in FIGS. 6a-6f.

TABLE II

Prostate plan goals and results.

| Regions | Acceptance criteria | $N_t = 18$ | $N_t = 23$ | $N_t = 29$ | $N_t = 35$ | $N_t = 45$ | $N_t = 48$ |
|---|---|---|---|---|---|---|---|
| PTV | % vol > 78 Gy ≧ 95 | 95.0 | 95.0 | 95.0 | 95.0 | 95.0 | 95.0 |
| Rectum | % vol > 40 Gy ≦ 35 | 56.5 | 44.3 | 38.2 | 33.3 | 31.0 | 30.0 |
|  | % vol > 65 ≦ 17 | 13.8 | 12.9 | 10.7 | 9.8 | 9.7 | 9.4 |
|  | vol > 79.6 Gy ≦ 1 cc | 0.50 cc | 1.42 cc | 1.27 cc | 0.54 cc | 0.81 cc | 0.87 cc |
| Bladder | % vol > 40 Gy ≦ 50 | 46.5 | 38.8 | 29.1 | 24.3 | 21.3 | 19.1 |
|  | % vol > 65 Gy ≦ 25 | 11.1 | 9.3 | 8.1 | 7.9 | 7.5 | 6.9 |

TABLE II-continued

Prostate plan goals and results.

| Regions | Acceptance criteria | $N_t = 18$ | $N_t = 23$ | $N_t = 29$ | $N_t = 35$ | $N_t = 45$ | $N_t = 48$ |
|---|---|---|---|---|---|---|---|
| Femoral heads | % vol > 45 Gy ≦ 1 | 0.08 | 0.30 | 0.20 | 0.15 | 0.03 | 0 |
| Body | vol > 82.7 Gy ≦ 1 cc | 0.65 cc | 0.46 cc | 1.61 cc | 0.73 cc | 0.96 cc | 0.85 cc |
|  | MUs (2 Gy fr) | 334 | 334 | 342 | 343 | 347 | 350 |

% vol > x Gy: percentage of the volume that receives more than x Gy dose;
vol > x Gy: size of the volume that receives more than x Gy dose.

The total number of Pareto efficient points is mainly determined by the user-defined values of $s_1$ and $s_2$ as shown in FIG. 1. Note that, for a better illustration, the complete Pareto frontier was calculated in FIG. 2a. In reality, it is not necessary to compute all the Pareto efficient points, and calculations of many clinically unacceptable Pareto efficient points can be avoided to improve the computation efficiency. For example, if the Pareto efficient points between the anchor points are calculated from a small $\phi_1$ to a large $\phi_1$, the multiobjective optimization can stop when the plan first becomes clinically unacceptable, i.e., when $N_t=31$.

IMRT inverse planning is to obtain the best possible fluence profiles/maps that produce a desired/prescribed dose distribution. This is inherently an underdetermined problem and thus has no unique solution. Indeed, in inverse planning, a clinically satisfactory dose distribution for a given case can generally be achieved using different sets of fluence maps. In other words, there are many fluence maps that can yield a sensible IMRT treatment plan. Each of these "optimal" solutions has its pros and cons. A practical challenge is to find the solution that best balances the conformality of the final dose distribution and the sparsity of the fluence maps. The current invention provides an effective way of finding the optimal IMRT solutions with sparse or piecewise constant fluence maps.

Using compressed sensing, according to the invention, the planning as a multiobjective optimization problem is modeled, with one objective to quantify the dose performance and the other one to measure the sparsity of the solution. The algorithm has a form of convex optimization, with an ability to optimize the number of segments without compromising the dose performance in radiation therapy treatment. A method of calculating the Pareto frontier is also provided. Pareto efficient solutions are evaluated using clinical acceptance criteria, and the satisfactory plan with the smallest number of segments is chosen as the final solution. The performance of the algorithm is demonstrated using a prostate study. The result shows that the proposed method greatly reduces the number of segments without compromising the clinical performance of the treatment plan.

Figure 7:
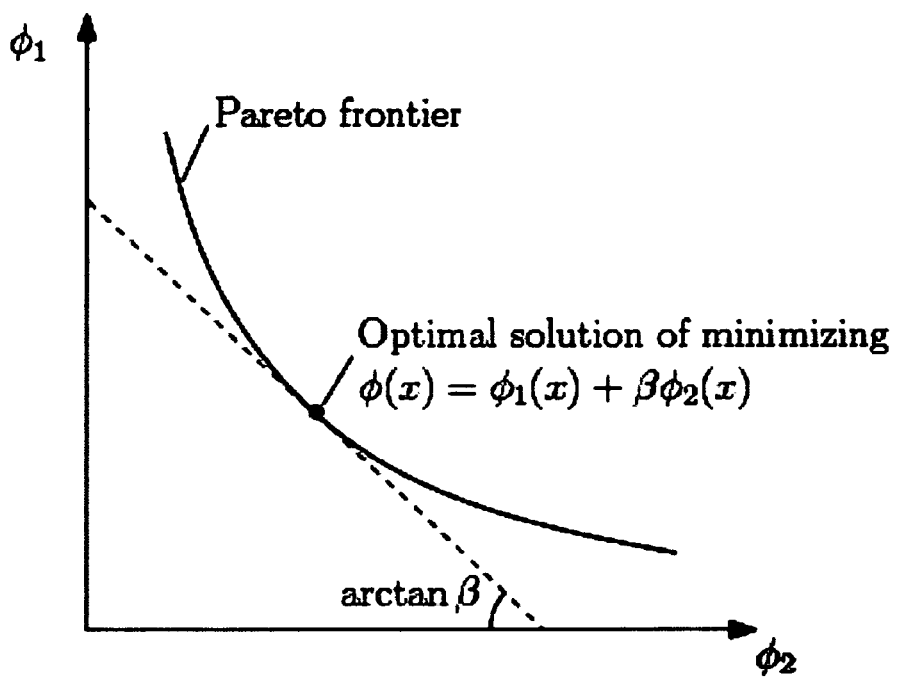
FIG. 7 shows the optimal solution is the Pareto efficient point on the Pareto frontier at which the tangent has a slope of −β, according to one embodiment of the invention.

Calculation of the Pareto frontier is one solution to a multiobjective optimization problem. Other standard methods can also be used here. For example, we can combine the two objectives and consider the L-1 norm as a regularization term with a user-defined penalty weight of $\beta$. The optimization problem is then converted to a quadratic programming. As shown in FIG. 7, the optimal solution obtained using this method is the Pareto efficient point on the Pareto frontier at which the tangent has a slope of $-\beta$. The optimal value of $\beta$ can be determined by balancing the trade-off between the objectives. For example, some researchers use an L-curve analysis to first calculate the point of maximum curvature in FIG. 7 and then find the corresponding $\beta$ as the optimal value.

The multiobjective approach according to one embodiment of the invention provides a more general solution without introducing the parameter $\beta$.

The traditional beamlet-based optimization method is sensible from a mathematical point of view, as it is conceptually intuitive, computationally tractable, and yields the best possible dose distribution for a given objective function. However, because of the complete ignorance of issues related to the MLC-based dose delivery, this approach usually results in a large number of segments and leads to a plan inefficient to delivery. The large number of segments using a traditional beamlet-based method is due to the high complexity of the optimized beamlet intensity map. In the literature, many algorithms have been proposed to ameliorate this problem using smoothing techniques. Typical examples use an additional term of sum of derivative squares, which are often referred to as quadratic smoothing or regularization in the theory of convex optimization. Although these algorithms suppress the complexity of the beamlet intensity map, they do not achieve piecewise constant beamlet intensity maps. As shown in the comparisons of FIGS. 2a-2b and FIGS. 3a-3b, the smoothing on the sharp edges at the aperture boundaries makes it difficult to further reduce the number of segments. According to the invention a general framework of multiobjective optimization is formulated with a focus on the piecewise constant feature of an actual fluence map and relate the number of segments to the sparsity of the derivative of a beamlet intensity map. Compressed sensing techniques are used to solve the problem, since it is able to achieve a heuristic sparse solution.

Segment-based optimization algorithms achieve small numbers of segments by imposing the physical constraints of beam apertures in the optimization. In a sense, this is similar to what many investigators have done in the context of 3D conformal therapy plan optimization, where the machine related parameters such as the beam weights and wedge angles are optimized. These algorithms eventually search in a space of all possible segments for a sparse optimal solution. Since such a space is non-convex, random search algorithms, such as simulated annealing, are commonly employed. The computation is therefore intensive and a global optimal solution is not always guaranteed. Furthermore, most of the segment-based methods prefix the total number of segments to limit the size of search space and increase the search efficiency. Roughly speaking, these methods calculate only one point on the Pareto frontier as shown in FIG. 1, of which the $\phi_2(x)$ value is defined by the prefixed number of segments. As a result, the solution is most likely not clinically optimal. In the method of the current invention, compressed sensing is used to encourage a sparse solution and formulate a multiobjective optimization problem. The optimization is still convex, and therefore a Pareto optimal solution can always be obtained with a high computation efficiency.

According to one embodiment of the invention, novel systems and methods for enhancing the performance of intensity modulated radiation therapy (IMRT) are provided.

According to one embodiment of the invention, an RT planning and delivery scheme that is capable of producing tomotherapy-like dose distribution with a delivery efficiency comparable or even better than current VMAT.

The RT modality of the current embodiment, coined to as dense angular and sparse intensity sampled radiation therapy (DASIS-RT), is achieved by increasing the angular sampling of radiation beams while reducing the complexity of intensity modulation of each independent beam through elimination of dispensable segments with methods such as total-variation regularization described above. In the method of the current embodiment, the saved delivery time in MLC segment reduction is used to increase angular sampling. The gantry rotation from one position to the next will be made efficient by concatenating the beams during delivery.

Clinically, linac-based RT uses IMRT with 5~10 fixed-gantry beams or VMAT with 1~2 arcs for delivering conformal dose distribution. The former achieves a reasonable dose distribution by heavy modulation of intensity profiles. The level of intensity modulation is generally unconstrained and the resultant number of segments is huge in the realization of an optimized fluence map. The conformality of the achievable dose distribution is often limited by the limited number of beams (or the sparse angular sampling). On the other hand, the latter, VMAT, produces conformal dose distribution by continuously rotating the gantry while modulating the aperture shape and weight. Fundamentally, VMAT is a special form of IMRT with a large number of incident beams, each having an aperture shape and intensity, subjecting to the machine delivery constraints. Because VMAT is limited to one aperture per gantry angle (unless multiple arcs are employed), it often does not provide the needed intra-beam intensity modulation in some or all directions. The use of multiple arcs is an option, but it may defeat the purpose of fast delivery of VMAT. Also, in one embodiment, a need for more apertures may not apply to every direction. Increasing the number of beams in traditional fixed-gantry IMRT and or increasing the number of arcs significantly prolong the treatment delivery and are thus not practical. The current embodiment is a delivery scheme with dense angular sampling but sparse and field-specific intensity modulation. In this method, the increased delivery time due to increased angular sampling is partially or fully compensated by the time gain of sparsely modulated beam delivery. The approach allows one to optimally distribute the delivery time among the sampling of beam angles and MLC segments to achieve the best possible dose distribution for a given patient.

Regardless of the specific delivery scheme, the fundamental of modern RT is dominated by a variant statement of the classical Shannon-Nyquist theorem: in order to control maximally the dose at each individual voxel, the number of independent beam parameters should generally be comparable to the number of voxels. For efficient maneuver of the dose on a regional level, an over-determined system is desired. In reality, neither fixed-gantry IMRT nor VMAT satisfies this condition for a broad spectrum cases, leading to sub-optimal treatment plans. The former may not have enough angular sampling whereas the latter may fall short in providing sufficient number of apertures. Angular sampling of beams is important to the dose, whereas intensity modulation of a beam is important for intra-beam tradeoff. From mathematical point of view, tomotherapy with slice-by-slice modulation with binary collimator is an ideal approach because it fully utilizes intensity and angular space to produce best possible dose. The embodiment of dense angular and sparse intensity sampled radiation therapy (DASIS-RT) produces tomotherapy-like dose distribution with MLC-based cone beam delivery. It greatly increases the delivery efficiency as compared with tomotherapy while improving the confamality and maneuverability of the resultant dose distribution as compared with traditional sparse angular and dense intensity sampled IMRT. The technique uses a large number of intensity-regularized beams (e.g., 10~100) (or a combination of discrete beams with regularized intensity and segmented arcs) to increase angular sampling and maintain the overall delivery time to within a practically acceptable limit.

Advantages of the current embodiment include:
(1) Effectively avoid undersampling of the involved voxels, thus providing an increased degree of freedom for improving and/or maneuvering the resultant dose distribution.
(2) Combined increase of sampling in angular and intensity space.
(3) Compared to VMAT, the approach makes dual- or multiple energy treatment possible.
(4) Imaging can be performed during switch from one gantry angle to another.
(5) Making fine-tuning of IMRT plan easy because of increased sampling.
(6) Applicable for delivery of high dose rate flattening filter-free (FFF) beams. The regularization of inverse planning in this case is done in the FFF functional domain.
(7) Delivery scheme with a combination of segmented arc(s) and fixed gantry beams is a special case of this scheme.
(8) Easy to perform quality assurance (QA).
(9) The approach is also applicable to non-linac machines such as Cobalt machine (with one or more sources).
(10) Mixed energy treatment is easy (which is not the case when VMAT is used).

Variations of the current embodiment include extending to non-linac based radiation therapy, such as Colbalt-60 machine with one or multiple sources. Further, the embodiment combines segmented arcs and beams at discrete gantry angles.

The current embodiment, is capable of producing tomotherapy-like dose distribution with a delivery efficiency comparable or even better than current VMAT. An increased angular sampling of radiation beams while reducing the complexity of intensity modulation of each independent beam through elimination of dispensable segments with methods such as total-variation regularization is provided. In this method, the saved delivery time in MLC segment reduction is used to increase angular sampling. The gantry rotation from one position to the next will be made efficient by concatenating the beams during delivery.

Radiation therapy with high dose rate and flattening filter-free (FFF) beams has the potential advantage of greatly reduced treatment time and out-of-field dose. Because current inverse planning algorithms are not customized for beams with non-uniform incident profiles and the resultant IMRT plans are often inefficient in delivery, a total-variation regularization (TVR)-based formalism is provided by taking the inherent shapes of incident beam profiles into account.

The TVR-based inverse planning formalism of one embodiment is established for IMRT with non-uniform beam profiles. A TVR term is introduced into the objective function, which encourages piecewise constant fluence in the non-uniform FFF fluence domain. The algorithm was demonstrated when applied to a lung and a prostate case and its performance is evaluated by comparing the resulting plans to those obtained using a conventional beamlet-based optimization (BBO).

For the prostate case, the algorithm produced acceptable dose distributions with only segments, while the conventional BBO requires 114 segments. For the lung case, the method generated similar coverage of target volume and sparing of the organs-at-risk as compared with BBO, but with a markedly reduced segment number.

TVR-based optimization in non-flat beam domain provides an effective way to maximally leverage the technical capacity of radiation therapy with FFF fields. The technique generates effective IMRT plans with improved dose delivery efficiency without deterioration of the dose distribution.

The IMRT planning with flattened beams according to the current invention, provide total-variation based compressed sensing (CS) technique to better balance the tradeoff between fluence modulation complexity and plan deliverability. This CS-based planning technique naturally accounts for the interplay between planning and delivery and balances the dose optimality and delivery efficiency in a controlled way. As discussed, the central idea of the approach is to introduce an L-1 norm to encourage piece-wise constant fluence maps, such that the number of beam segments is minimized, while using a quadratic term to ensure the goodness of dose distribution. The method produces highly conformal IMRT plans with sparse fluence maps. This framework is applicable to FFF-based IMRT treatment planning. By properly introducing the total-variation regularization, the method greatly facilitates the search for fluencies that are piece-wise constant in a domain defined by the basis function of the non-uniform incident beams. According to one embodiment of the invention, a TVR-based inverse planning method is provided for IMRT with FFF beams. For this purpose, an L-1 objective function specific to the known non-flat beam profile characteristics is constructed. Optimization of the system provides non-flat beam IMRT solutions that are piece-wise constant in the selected FFF-domain and thus efficiently deliverable.

According to the current embodiment, each incident beam is divided into a collection of 0.5×0.5 cm² beamlets. The linear relationship (1) between the dose distribution, d, and beam fluence maps, x, is utilized to calculate the dose delivered to a patient. The beamlet kernel matrix, A, which corresponds to pencil beam contributions from each voxel, is pre-calculated using the VMC++ Monte Carlo method through the CERR interface.

The profile of a FFF beam can be generally expressed as $$U = 1 - (1/R) * \sqrt{u^2 + v^2} \tag{16}$$

where U is the beam intensity, (u, v) are the beamlet index, R is the base radius that describes the level of non-flatness of the beam. The general non-uniform beam has a cone-shaped profile, and the dose decreases with increased distance from the central axis. For a non-uniform beam profile with R=80 cm the dose is less than 10% at 7 cm off the central axis (~8.8%), which is in good agreement with previous studies.

Figure 8:
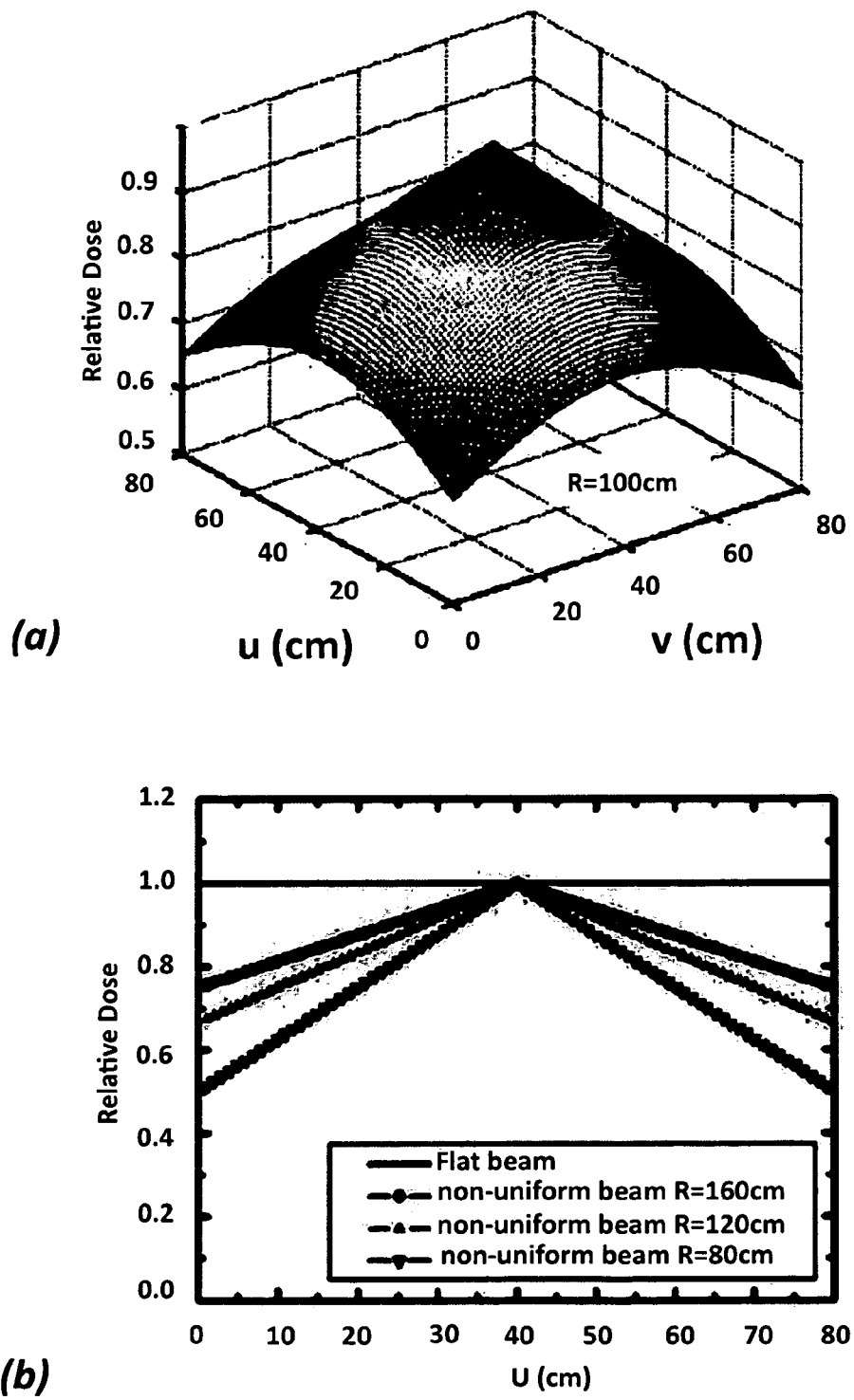
FIG. 8a-8b show the flat and non-uniform beam profiles with varying base radii, according to one embodiment of the invention.

When R=∞, Eq. (16) describes a conventional uniform beam. FIG. 8a-8b show the flat and non-uniform beam profiles with varying base radii, where FIG. 8a shows a radially symmetric feature of a non-uniform beam is presented in 3D, and FIG. 8a shows a one-dimensional non-uniform beam profile cross sections with three different base radii (R=80 cm/120 cm/160 cm) and the flat beam cross section. The profile with R=80 cm corresponds to the 6MV FFF beam from the TrueBeam linear accelerator. The general non-uniform beam profile is used to transform a non-uniform beam into a flat beam (i.e., one may view the transformation as a voxel specific scaling).

A total-variation regularization (TVR) term is introduced in the objective function to accommodate the inherent profile of the non-uniform fluence to encourage piecewise constant fluence in the non-uniform fluence domain. The optimization problem including the TVR term is expressed as Minimize $$\sum_{i=1}^{N} r_i (A_i x - d_i)^T (A_i x - d_i) + \tag{17}$$

$$\beta \sum_{f=1}^{Nf} \sum_{u=2}^{Nu} \sum_{v=2}^{Nv} (|X_{u,v,f} - X_{u,v-1,f}| + |X_{u,v,f} - X_{u,v-1,f}|)$$

subject to $$x \geq 0$$

$$X = U^{-1} x$$

where x is the beamlet intensity, X is the beamlet intensity in the flat fluence domain (which is related to the beamlet intensity by a transformation matrix, $U^{-1}$ that normalizes a non-flat beam to a flat beam according to the beam profile), $r_i$ is the importance factor, β is an empirical regularization parameter, $d_i$ is the desired dose, Nu and Nv are the total numbers of discretization perpendicular and along the MLC leaf motion direction, and Nf is the number of fields. The algorithm of the current embodiment is implemented in Matlab and uses the MOSEK software package.

The performance of the current embodiment is demonstrated on a prostate and lung case. For the prostate patient, five fields with gantry angles of 0°, 70°, 145°, 215°, 290° were used. A dose of 78 Gy is prescribed to the planning target volume (PTV). Six field angles (30°, 60°, 90°, 120°, 180°, 210°) were used to generate the lung IMRT plan, and the prescribed dose to the PTV is 74 Gy. All plans were normalized so that 95% of the PTV volume received the prescribed dose. For efficient computation, the pixel size of the CT images was downsampled to 3.92×3.92×2.5 mm³ for the beamlet kernel and dose calculations. The performance of the current embodiment was evaluated by comparing against 120 IMRT plans obtained using conventional beamlet-based optimization without TVR.

The level of beam modulation complexity of an IMRT plan, which is a general measure of the deliverability, can be evaluated using the modulation index (MI), where series of 1D fluence profiles were introduced in 2D planning. Here, the MI is modified to measure the modulation complexity of 2D fluence maps as described below:

$$\Delta_u = \text{abs}(x_{u,v,f} - x_{u-1,v,f}) \tag{18}$$

$$\Delta_v = \text{abs}(x_{u,v,f} - x_{u,v-1,f})$$

$$N(f; \Delta_u \text{ and } \Delta_v \succ f\sigma)$$

$$f = 0.01, 0.02 \ldots 2$$

$$z(f) = \left( \frac{1}{(Nu-1) * Nv + Nu * (Nv-1)} \right) * N(f)$$

$$MI = \int_0^{0.5\sigma} z(f) df$$

Figure 9:
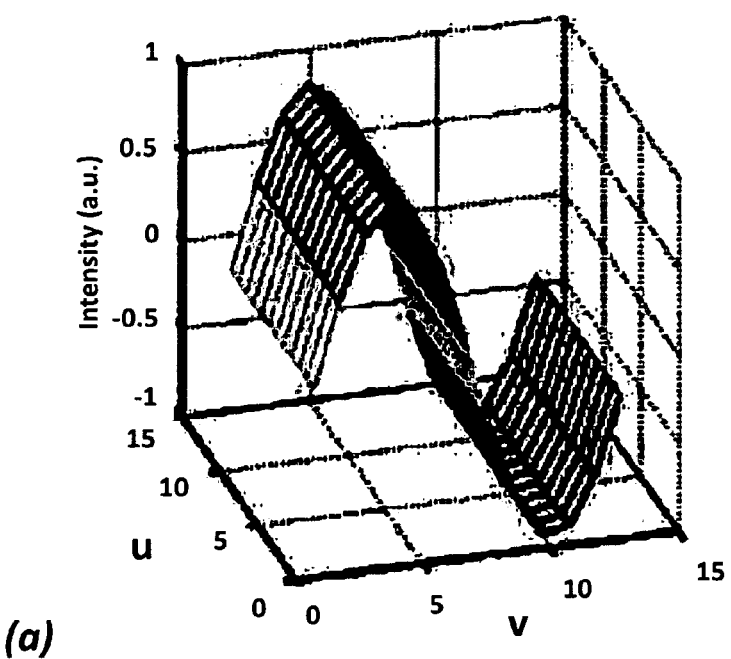
FIGS. 9a-9b show 2D intensity-modulated beam examples of 12×13 beamlets, according to one embodiment of the invention.
Figure 9:
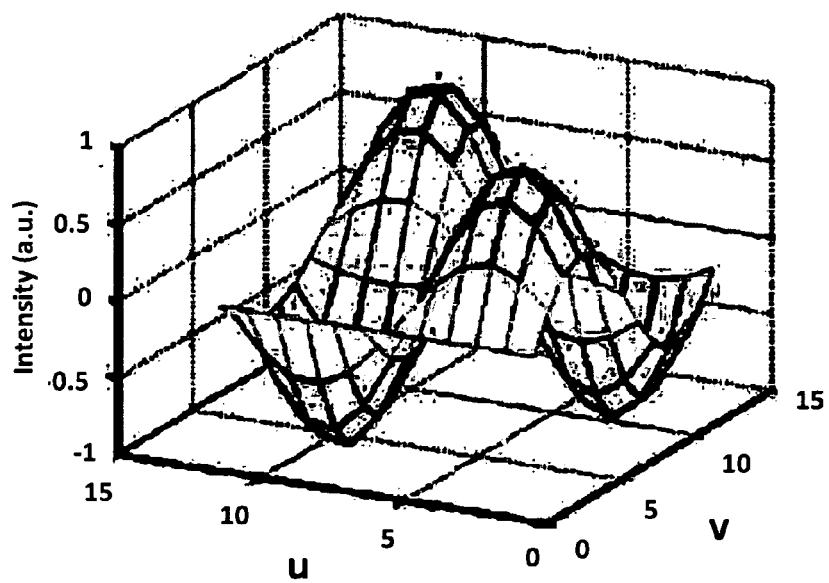

Here, φ is the standard deviation of the beamlet intensities and Δ is the intensity change between adjacent beamlets. N is the number of adjacent beamlet intensity changes satisfying the test condition $\Delta_u$ and $\Delta_v \succ f\sigma$, where f=0.01, 0.02 ... 2. For illustration purposes, 2D intensity-modulated beam examples of 12×13 beamlets are shown in FIGS. 9a-9b, where FIG. 9a shows a single cycle of a sine wave along the v direction, and FIG. 9b shows a single cycle of a sine wave along both u and v directions.

Figure 10:
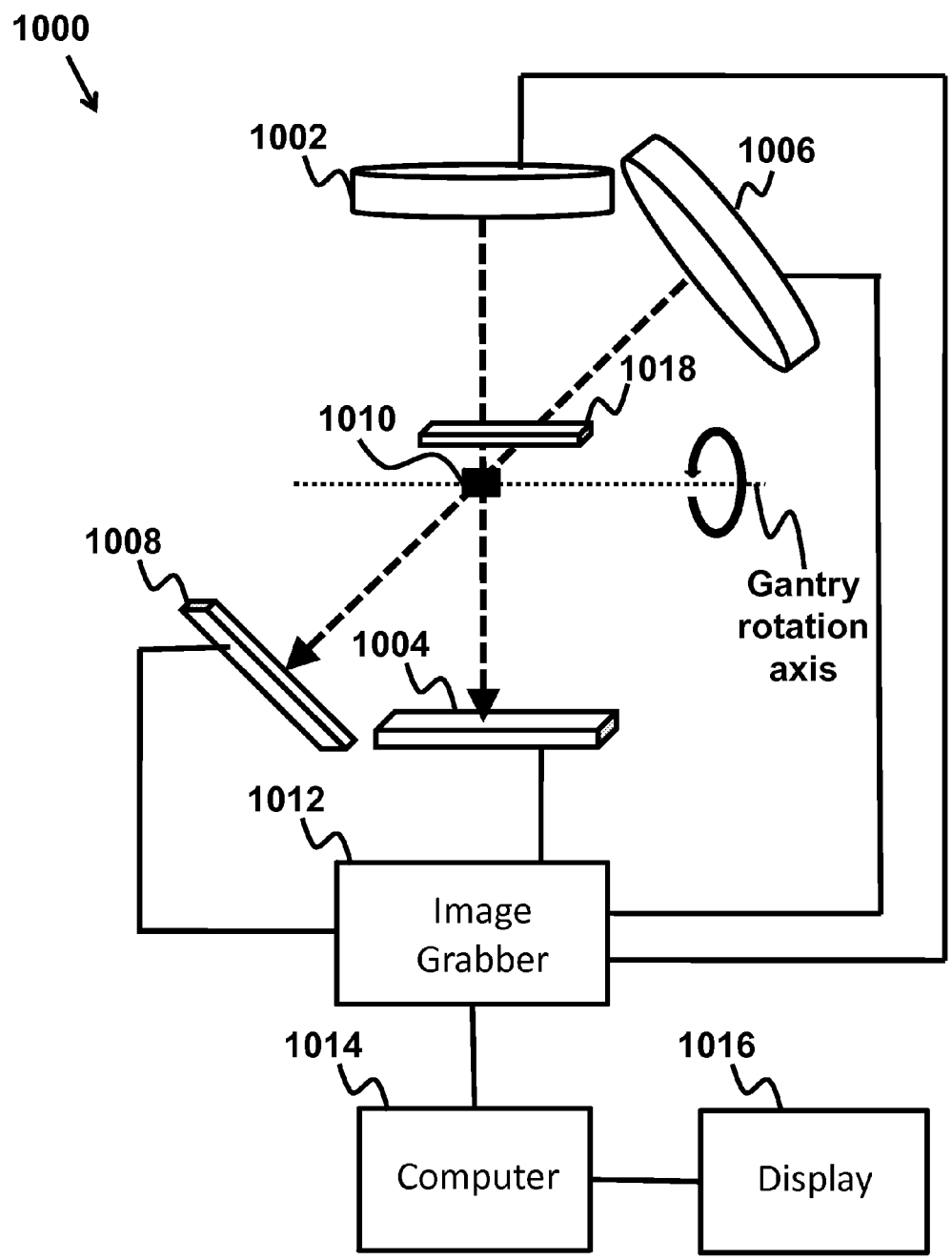
FIG. 10 shows a schematic drawing of the apparatus used for implementing the method OF reducing a total number of beam segments in a dose distribution for a radiation therapy field, according to one embodiment of the invention.

FIG. 10 shows a schematic drawing 1000 of the apparatus used for implementing the method of reducing a total number of beam segments in a dose distribution for a radiation therapy field, according to one embodiment of the invention. As shown, a first radiation therapy source 1002 and a first detector 1004 along with a second radiation therapy source 1006 and a second detector 1008 are provided to establish dose distribution to an initial 3D target 1010 position. The target position monitoring and dose distribution is in combination with an online-updated characterization of target 1010 motion, where the online-updated characterization includes an image grabber 1012, a computer 1014 and display 1016. The computer 1014 operates a MLC 1018 and dose distributions according to a multiobjective radiation therapy treatment plan, where the multiobjective radiation therapy treatment plan includes a radiation beam dose performance objective and a fluence map sparsity objective, and providing a Pareto frontier of tradeoff criteria between the beam dose performance and a total number of radiation beamlets of the multiobjective radiation therapy treatment plan using the suitably programmed computer, where an achieved set of radiation beam dose distributions associated with efficiency points of the Pareto frontier are evaluated using a clinical acceptance criteria, where a clinically acceptable radiation beam dose distribution having a smallest number of the radiation beamlets is a final solution for the multiobjective radiation therapy treatment plan.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example a squared sum of the intensity derivatives, a regularization based on decomposition of the fluence maps with respect to a given set of basis functions or principal components.

All such variations are considered to be within the scope and spirit of the present invention as defined by the following claims and their legal equivalents.

What is claimed:

1. A method of reducing a total number of beam segments of radiation therapy fields, comprising:
    a. providing a multiobjective radiation therapy treatment plan using a suitably programmed computer, wherein said multiobjective radiation therapy treatment plan comprises a radiation beam dose performance objective and a fluence map sparsity objective; and
    b. providing a Pareto frontier of tradeoff criteria between said beam dose performance and a total number of radiation segments of said multiobjective radiation therapy treatment plan using said suitably programmed computer, wherein an achieved set of radiation beam dose distributions associated with efficiency points of said Pareto frontier are evaluated using a clinical acceptance criteria, wherein a clinically acceptable radiation beam dose distribution having a smallest number of said radiation segments comprises a final solution for said multiobjective radiation therapy treatment plan.

2. The method of claim 1, wherein said radiation therapy treatment plan comprises intensity modulated radiation therapy or arc therapy.

3. The method of claim 1, wherein radiation beamlets are disposed in a concatenated orientation during beam delivery.

4. The method of claim 1, wherein said efficiency points of said Pareto frontier are provided by an optimization function, wherein said optimization function comprises a regularization-based algorithm operated on a suitably programmed computer, wherein said regularization-based algorithm comprises:
    a. a total-variation term or objective, a regularization term or a method of providing piece-wise connected fluence maps in an optimization objective function; and
    b. a multi-leaf collimator or a CyberKnife collimator aperture rectification algorithm.

5. The method of claim 4, wherein said piece-wise connected fluence map comprises a piece-wise constant map, wherein said piece-wise connected map comprises a cone-shaped fluence, a constant slope or a given functional form.

6. The method of claim 1, wherein optimization of said multiobjective radiation therapy treatment plan comprises:
    a. using a convex or non-convex optimization, a regularization term or a method for providing piece-wise connected fluence maps, wherein said convex optimization is disposed to enforce beam sparsity of said final solution, wherein said number of beam segments is minimized; and
    b. using a quadratic term or other form of said objective function to quantify said radiation dose performance.

7. The method of claim 1, wherein an angular space delivery comprises a combination of fixed-gantry beams and rotational arc beams.

8. The method of claim 1, wherein beamlets are determined using computed tomography (CT) images, treatment machine settings, and radiation beam geometry.

9. The method of claim 1, wherein said multiobjective radiation therapy treatment plan further comprises a multi-leaf collimator (MLC) based IMRT delivery, wherein said MLC based IMRT delivery comprises:
    a. a uniformity constraint comprising a condition where an intensity map of a beam aperture is uniform inside an open area of said MLC and zero elsewhere; and
    b. a connectivity constraint comprising a condition where nonzero intensity areas of one said beam aperture are connected in a direction of leaf pairs of said MLC.

10. The method of claim 1, wherein said radiation source comprises fixed-gantry IMRT or a hybrid of fixed-gantry IMRT and rotational arc therapy.

11. The method of claim 1, wherein said clinical acceptance criteria comprises inspection of dose volume histograms and dose distributions in a treatment plan.

* * * * *